US009980659B2

(12) United States Patent
Sadeghian-Motahar et al.

(10) Patent No.: US 9,980,659 B2
(45) Date of Patent: May 29, 2018

(54) BIO-POTENTIAL SENSING MATERIALS AS DRY ELECTRODES AND DEVICES

(71) Applicant: NeuroRex Inc., Houston, TX (US)

(72) Inventors: Seyedhesam Sadeghian-Motahar, Houston, TX (US); Robert Kelley Bradley, Houston, TX (US)

(73) Assignee: NeuroRex Inc., Houston, TX (US)

( * ) Notice: Subject to any disclaimer, the term of this patent is extended or adjusted under 35 U.S.C. 154(b) by 232 days.

(21) Appl. No.: 14/827,530

(22) Filed: Aug. 17, 2015

(65) Prior Publication Data

US 2016/0089045 A1    Mar. 31, 2016

Related U.S. Application Data

(60) Provisional application No. 62/056,421, filed on Sep. 26, 2014.

(51) Int. Cl.
*H01B 1/22* (2006.01)
*A61B 5/00* (2006.01)
(Continued)

(52) U.S. Cl.
CPC .............. *A61B 5/04* (2013.01); *A61B 5/0531* (2013.01); *A61B 5/441* (2013.01); *A61B 5/6839* (2013.01);
(Continued)

(58) Field of Classification Search
CPC ... H01B 1/00; H01B 1/20; H01B 1/22; H01B 1/24; A61B 5/04087; A61N 1/00492; H01R 4/04
See application file for complete search history.

(56) References Cited

U.S. PATENT DOCUMENTS 4,324,680 A * 4/1982 Kubota .................. G01R 31/16
                                                  252/182.1
5,207,950 A * 5/1993 Ehrreich ................. C08K 9/02
                                                  252/512
(Continued)

FOREIGN PATENT DOCUMENTS

WO     2003028039 A1    4/2003
WO     2012140629 A1    10/2012

OTHER PUBLICATIONS

Shin et al "Elastomeric conductive composites based on carbon nanotube forests", Adv. Mater. 2010, 22, 2663-2667. (Year: 2010).*

(Continued)

*Primary Examiner* — Mark Kopec
(74) *Attorney, Agent, or Firm* — Equip Law Group; Christopher Quan

(57) ABSTRACT

This invention is directed to materials and devices for sensing bio-potential signals from animals, particularly to sensing bio-potential signals to monitor humans in the medical field. In general, bio-potential sensors may be attached to the body of an animal, such as a human, in order to receive bio-potential signals such that information about the bioelectrical properties of the cells and/or tissues of the animal may be gathered. The bio-potential sensor may generally include a dry electrode that may be placed in contact with the skin of an animal to receive bio-potential signals from the animal. A dry electrode may generally include an electrically conductive solid material which may conduct electrical signals from an animal.

6 Claims, 1 Drawing Sheet

(51) Int. Cl.
*A61B 5/04* (2006.01)
*A61B 5/053* (2006.01)

(52) U.S. Cl.
CPC ............ *H01B 1/22* (2013.01); *A61B 2562/14* (2013.01); *A61B 2562/164* (2013.01); *A61B 2562/222* (2013.01); *A61B 2562/227* (2013.01)

(56) References Cited

U.S. PATENT DOCUMENTS

| | | | | |
|---|---|---|---|---|
| 5,565,143 | A * | 10/1996 | Chan | ............... H01B 1/20 252/514 |
| 6,177,482 | B1 * | 1/2001 | Cinelli | ............... A61F 13/82 428/355 R |
| 6,497,949 | B1 * | 12/2002 | Hyde | ............... B32B 7/12 428/355 AC |
| 6,710,099 | B2 * | 3/2004 | Cinelli | ............... A61L 15/58 523/105 |
| 8,552,299 | B2 * | 10/2013 | Rogers | ............... H01L 21/4867 174/254 |
| 8,608,984 | B1 | 12/2013 | Taranekar | |
| 2005/0032952 | A1 * | 2/2005 | Bonfanti | ............... C09J 131/04 524/306 |
| 2005/0096574 | A1 * | 5/2005 | Wibaux | ............... H05B 3/342 602/2 |
| 2011/0016675 | A1 * | 1/2011 | Mayers | ............... C09J 7/00 24/450 |
| 2012/0046535 | A1 | 2/2012 | Lin | |
| 2012/0154980 | A1 | 6/2012 | Kinlen | |
| 2013/0102874 | A1 | 4/2013 | Chi | |
| 2014/0058243 | A1 | 2/2014 | Lin | |
| 2017/0098488 | A1 * | 4/2017 | Sugita | ............... H01B 1/24 |
| 2017/0137558 | A1 * | 5/2017 | Faust | ............... C08G 18/6204 |

OTHER PUBLICATIONS

Li et al "Toward a stretchable, elastic, and electrically conductie nanocomposite. morphology and properties of poly[styrene-b-(ethylene-co-butylene)-b-styrene]/multiwalled carbon nanotube composites fabricated by high-shear processing", Macromolecules 2009, 42, 2587-2593. (Year: 2009).*

* cited by examiner

BIO-POTENTIAL SENSING MATERIALS AS DRY ELECTRODES AND DEVICES

CROSS-REFERENCE TO RELATED APPLICATIONS

This application claims the benefit and priority of U.S. provisional patent application Ser. No. 62/056,421, filed Sep. 26, 2014, entitled, "BIO-POTENTIAL SENSING MATERIALS AS DRY ELECTRODES AND DEVICES", the contents of which is hereby incorporated by reference its entirety.

COPYRIGHT NOTICE

A portion of the disclosure of this patent document contains material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

FIELD OF THE INVENTION

This invention relates to materials and devices for sensing bio-potential signals from animals, particularly to sensing bio-potential signals to monitor humans in the medical field.

BACKGROUND OF THE INVENTION

The use of electrodes to sense and measure bio-potential signals is widely practiced in the medical field as part of the various diagnostic tools such as electrocardiography (ECG/EKG) for monitoring heart function, electromyography (EMG) for monitoring muscle activity and electroencephalography (EEG) for studying brain activity and the like. The prior art for these techniques is to use a metal electrode which is in contact with its ionic form through a gel-bound electrolyte which then contacts the skin. A commonly used system of this type is the "wet" electrode which is typically an Ag/AgCl electrode. These systems suffer from many disadvantages documented in literature such as the requirement of skin preparation including removal of hairs by shaving, and removal of the stratum corneum by scrubbing. Furthermore, wet electrodes commonly cause skin irritation in persons with sensitive skin.

Licata and Mitchell disclosed the use of soft elastomeric bristles filled with a conductive liquid as a biopotential sensor (see U.S. Pat. No. 6,510,333). The technique of U.S. Pat. No. 6,510,333 does not require preparation of the skin, however it does require liquid to be in the bristles and also recommends an abrasive scrubbing of the skin in order to eliminate resistance from the surface of the skin. The bristles also require refilling throughout their lifetime which can be an added inconvenience to the user.

Schmidt, Lisy, Skebe, and Prince from Orbital Research Inc. (U.S. Pat. No. 7,032,301) disclosed a dry physiological recording electrode that does not require any skin preparation. This assembly requires constant contact with the skin. To ensure constant contact the assembly pierces the skin in order to obtain a biopotential signal which can cause pain and discomfort to the user.

Lin and Liao (see U.S. Pat. Pub. No. 2014/0058243) disclosed a dry electrode device and fabrication methods. However, their electrode uses multiple spring loaded pogo pins, and the metal probes cause discomfort to user and can scratch the head. Additionally, monitoring a moving subject is a challenge as the spring probes move up and down and the skin-electrode impedance changes, which causes noise in the signal.

Chi from Cognionics Inc (see U.S. Pat. Pub. Nos. 2013/0102874 and 2013/0066185) disclosed a dry electrode with a mechanism for noise reduction on a moving subject. However, their dry flex electrode can experience several issues, such as a lack of bandwidth, higher electrode impedance (50-300 kohm) than the accepted standard range for medical EEG recording (less than 5 kohm) and no MRI compatibility.

SUMMARY OF THE INVENTION

This invention is directed to materials and devices for sensing bio-potential signals from animals, particularly to sensing bio-potential signals to monitor humans in the medical field. In general, bio-potential sensors may be attached to the body of an animal, such as a human, in order to receive bio-potential signals such that information about the bioelectrical properties of the cells and/or tissues of the animal may be gathered. The bio-potential sensor may generally include a dry electrode that may be placed in contact with the skin of an animal to receive bio-potential signals from the animal. A dry electrode may generally include an electrically conductive solid material which may conduct electrical signals from an animal.

In one aspect of the present invention, the dry electrode of a bio-potential sensor may include a polymeric material which may be placed in contact with the skin and conductively linked to a connector. In some exemplary embodiments, the polymeric material may generally exhibit low electrical resistance, such as, for example, as measured by volume resistivity. The polymeric material may also be surface treated to improve (lower) its contact resistance for better signal conduction from the skin. The polymeric material may also generally exhibit mechanical properties such that the polymeric material may be easily extruded, injection molded, and/or otherwise be easily formed into an electrode. The polymeric material may also generally exhibit high elasticity and/or other mechanical properties such that the polymeric material may be conformed to non-uniform surfaces such as, for example, the skin.

In some exemplary embodiments, the polymeric material may be a copolymer which may include, for example, a modified polyolefin polymer. For example, a modified polyolefin polymer may include a block copolymer. The polymeric material may further include electrically conductive additives, fillers and/or monomers, such as metals, metal particles, non-metallic conductive particles, coated particles and/or any other appropriate conductive material.

In some exemplary embodiments, the polymeric material may include a polyolefin elastomer modified with a synthetic rubber block copolymer and an electrically conductive additive, filler and/or monomer.

In another aspect, the polymeric material may be fabricated into one of many forms, using any appropriate plastics processing method, such that it may be incorporated into a desired form of bio-potential sensor.

In a further aspect of the invention, the bio-potential sensor may have a generally continuous and/or substantially flat contact surface for interfacing with the skin or other tissue of an animal.

In another aspect of the invention, the bio-potential sensor may have an irregular and/or textured contact surface and/or feature. In some embodiments, the bio-potential sensor may include a contact surface with a plurality of leads, pins, and/or other forms of protrusions to, for example, aid in better contact with the skin and/or tissue of an animal. For example, protrusions, such as of a smaller size than the overall bio-potential sensor, may be desirable to contact the skin and/or tissue of an animal through fur, hair and/or other coverings where a continuous and/or substantially flat contact surface would have difficulty attaining contact.

In still another aspect of the invention, the bio-potential sensor may be designed for user comfort and/or safety such that it may be worn for extended periods and/or during normal activity without disrupting and/or harming the user. In some embodiments, the bio-potential sensor may generally have a low-profile form.

The present invention together with the above and other advantages may best be understood from the following detailed description of the embodiments of the invention illustrated in the drawings.

DETAILED DESCRIPTION OF THE INVENTION

The detailed description set forth below is intended as a description of the presently exemplified devices, methods and materials provided in accordance with aspects of the present invention, and it is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

Figure 1:
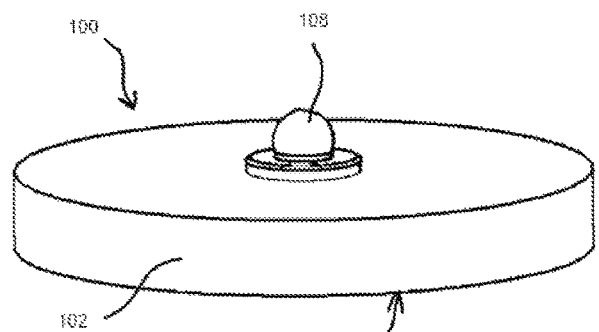
FIGS. 1 and 1a illustrate an embodiment of a bio-potential sensor with a contact surface.
Figure 1A:
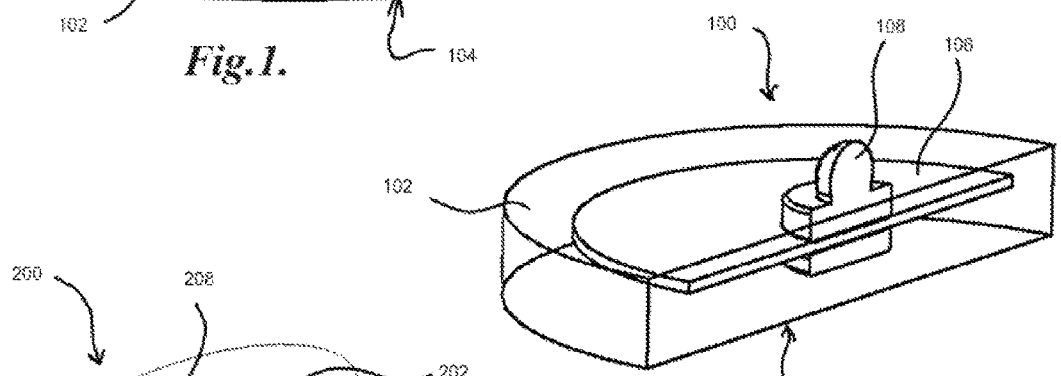

This invention is directed to materials and devices for sensing bio-potential signals from animals, particularly to sensing bio-potential signals to monitor humans in the medical field. In general, bio-potential sensors may be attached to the body of an animal, such as a human, in order to receive bio-potential signals such that information about the bioelectrical properties of the cells and/or tissues of the animal may be gathered. The bio-potential sensor may generally include a dry electrode that may be placed in contact with the skin of an animal to receive bio-potential signals from the animal. A dry electrode may generally include an electrically conductive solid material which may conduct electrical signals from an animal, as illustrated with the bio-potential sensor 100 of FIGS. 1 and 1a. FIG. 1a illustrates a see-through cross-sectional view of an example of a dry electrode bio-potential sensor 100. In one aspect of the present invention, the dry electrode of a bio-potential sensor 100 may include a polymeric material which may be placed in contact with the skin and conductively linked to a connector, as illustrated with polymeric material 102 in FIGS. 1 and 1a. In some exemplary embodiments, the polymeric material may generally exhibit low electrical resistance, such as, for example, as measured by volume resistivity.

In some exemplary embodiments, the polymeric material may exhibit volume resistivities of less than about 70 ohm-cm, preferably below 10 ohm-cm and more preferably below 3 ohm-cm.

In some exemplary embodiments, the polymeric material may exhibit low electrical impedance to produce a viable signal for use, such as, for example, as a passive EEG electrode.

The contact resistance of the polymeric material may be also improved (lowered) by means of a surface treatment such as, for example, plasma etching, ion bombardment, ozone exposure, wet chemical etch and/or other similar methods, such as to preferentially etch the polymeric material to expose conductive filler at the surface for contact with a user.

In some exemplary embodiments, the polymeric material may also generally exhibit mechanical properties such that the polymeric material may be easily extruded, injection molded, and/or otherwise be easily formed into an electrode.

The polymeric material may also generally exhibit high elasticity and/or other mechanical properties such that the polymeric material may be conformed to non-uniform surfaces such as, for example, the skin. In some exemplary embodiments, the hardness modulus and/or other mechanical properties of the polymeric material may be generally similar and/or nearly the same as those of an animal tissue, such as, for example, human skin. This may be desirable as the similar mechanical properties may aid in conforming of the polymeric material to the surface of the animal tissue, which may also include conforming during movement and/or mechanical deformation of the animal tissue, to aid in providing continuous contact.

In some exemplary embodiments, the polymeric material may also exhibit a hardness modulus of between about 1.0 MPa and about 7.0 MPa, and/or a durometer of about 30 to 95 on Shore A.

In some exemplary embodiments, the polymeric material may be a copolymer which may include, for example, a modified polyolefin polymer. For example, a modified polyolefin polymer may include a block copolymer. The polymeric material may further include electrically conductive additives, fillers and/or monomers. Other fillers and/or additives may also be utilized to modulate conductivity and/or other mechanical properties. Some of these other fillers and/or additives may also be inert.

In some exemplary embodiments, the polymeric material may include a polyolefin elastomer modified with a synthetic rubber block copolymer and an electrically conductive additive, filler and/or monomer. Examples of polyolefin elastomers may include, but are not limited to, polyisobutylene (PIB), ethylene propylene rubber (EPR), and ethylene propylene diene monomer (M-class) rubber (EPDM rubber). Examples of synthetic rubber block copolymers may include, but are not limited to, the examples given in Table 1 below:

TABLE 1

| ISO 1629 Code | Technical Name | Common Names |
| --- | --- | --- |
| ACM | Polyacrylate Rubber | |
| AEM | Ethylene-acrylate Rubber | |
| AU | Polyester Urethane | |
| BIIR | Bromo Isobutylene Isoprene | Bromobutyl |
| BR | Polybutadiene | Buna CB |
| CIIR | Chloro Isobutylene Isoprene | Chlorobutyl, Butyl |
| CR | Polychloroprene | Chloroprene, Neoprene |
| CSM | Chlorosulphonated Polyethylene | Hypalon |
| ECO | Epichlorohydrin | ECO, Epichlorohydrin, Epichlore, Epichloridrine, Herclor, Hydrin |
| EP | Ethylene Propylene | |
| EPDM | Ethylene Propylene Diene Monomer | EPDM, Nordel |
| EU | Polyether Urethane | |
| FFKM | Perfluorocarbon Rubber | |
| FKM | Fluoronated Hydrocarbon | Viton, Kalrez, Fluorel, Chemraz |
| FMQ | Fluoro Silicone | FMQ, Silicone Rubber |
| FPM | Fluorocarbon Rubber | |
| HNBR | Hydrogenated Nitrile Butadiene | HNBR |
| IR | Polyisoprene | (Synthetic) Natural Rubber |
| IIR | Isobutylene Isoprene Butyl | Butyl |
| NBR | Acrylonitrile Butadiene | NBR, Nitrile, Perbunan, Buna-N |
| PU | Polyurethane | PU, Polyurethane |
| SBR | Styrene Butadiene | SBR, Buna-S, GRS, Buna VSL, Buna SE |
| SEBS | Styrene Ethylene Butylene Styrene Copolymer | SEBS Rubber |
| SI | Polysiloxane | Silicone Rubber |
| VMQ | Vinyl Methyl Silicone | Silicone Rubber |
| XNBR | Acrylonitrile Butadiene Carboxy Monomer | XNBR, Carboxylated Nitrile |
| XSBR | Styrene Butadiene Carboxy Monomer | |
| YBPO | Thermoplastic Polyether-ester | |
| YSBR | Styrene Butadiene Block Copolymer | |
| YXSBR | Styrene Butadiene Carboxy Block Copolymer | |

Examples of electrically conductive fillers and/or additives may include, but are not limited to, carbon black, graphite, single-wall carbon nanotubes, multi-wall carbon nanotubes, double-wall carbon nanotubes, silver and/or silver chloride coated structures, such as nano-wires, metal fibers, metal nanoparticles, metal microplates, glass and/or silica microparticles, microplates and/or beads coated with a conductive material, and/or any other appropriate fillers, additives, modifications and/or combinations thereof. The electrically conductive fillers and/or additives may be present at varied concentrations, such as, for example, about: 1) carbon black—weight concentration 0.5-10%; 2) Multiwall carbon nanotube (MWCNT)—weight concentration 0-3%; 3) Single-wall carbon nanotube (SWCNT)—weight concentration 0-3%; 4) Double wall carbon nanotube (DWCNT)—weight concentration 0-3%; and 5) Silver, stainless steel, copper and/or other metallic particles weight concentration 0-5%.

In some embodiments, cross linking agents, such as, for example, peroxides, may be added to promote the flocculation of electrically conductive fillers and/or additives, such as carbon black, into conductive paths. Loading of cross-link agents may vary, for example, from about 2-18 wt %.

In another aspect, the polymeric material may be fabricated into one of many forms, using any appropriate plastics processing method, such that it may be incorporated into a desired form of bio-potential sensor. The polymeric material may also include processing aids, such as to improve melt-flow or dispersion of fillers, such as, for example, Armowax W440.

In a further aspect of the invention, the bio-potential sensor may have a generally continuous and/or substantially flat contact surface for interfacing with the skin or other tissue of an animal. FIGS. 1 and 1a illustrates an example of a bio-potential sensor 100 with polymeric material 102 having a generally continuous contact surface 104 to, for example, contact animal tissue such as, for further example, human skin. The polymeric material 102 may further be mounted, coated onto, overmolded onto and/or otherwise fixed to a structural element, such as a fabric and/or mesh screen, as illustrated with polymeric material 102 molded around screen 106 as shown in the cross-sectional view of FIG. 1a. The polymeric material 102 may generally interface electrically with a connector 108, such as by direct physical contact between the polymeric material 102 and the connector 108, or electrical connection, such as by a connecting wire or other conductive element between the two, which may relay bio-potential signals conducted through the polymeric material 102 to an instrument for measurement and/or detection.

The connector 108 may generally connect to a lead wire which may pass the electrical signal from the electrode to the amplifier electronics. The lead wire may generally be a standard metal wire (solid or braided). The connector 108 may also generally include features to provide adequate physical contact between the connector 108 and the polymeric material 102 such that electrical signals may pass from the polymeric material 102 to the connector 108 with minimal loss and/or resistance. For example, a mechanical fastening feature may be utilized to press the connector 108 onto the polymeric material 102 to establish a firm physical connection. Mechanical fastening may include, but is not limited to, metal snap connections, screws, grommeted connections, metal tubes crimped onto the polymeric material 102, clasps, clips, compression fittings, press fittings and/or any other appropriate mechanical fastening.

In another aspect of the invention, the bio-potential sensor may have an irregular and/or textured contact surface and/or feature. In some embodiments, the bio-potential sensor may include a contact surface with a plurality of leads, pins, and/or other forms of protrusions to, for example, aid in better contact with the skin and/or tissue of an animal. For example, protrusions, such as of a smaller size than the overall bio-potential sensor, may be desirable to contact the skin and/or tissue of an animal through fur, hair and/or other coverings where a continuous and/or substantially flat contact surface would have difficulty attaining contact. The contact surface may also include macroscopic and/or microscopic structures for better contact with tissue, such as skin. Further, the surface may be coated with conductive materials, which may include, but are not limited to, nano-silver wires and/or other conductive fibers (e.g. SWCNT, DWCNT, MWCNT, silver ink) such as to, for example, reduce surface resistivity. The surface of the electrode that contacts the skin may also be treated to create a sticky or tacky surface to improve stability and/or prevent movement of the electrode. This may be accomplished by, for example, addition of an adhesive, by a surface treatment and/or other appropriate additive that increases tack or adhesion.

In still another aspect of the invention, the bio-potential sensor may be designed for user comfort and/or safety such that it may be worn for extended periods and/or during normal activity without disrupting and/or harming the user. In some embodiments, the bio-potential sensor may generally have a low-profile form. For example, a low profile form may generally not protrude from the body significantly while the bio-potential sensor is attached. The low-profile form may thus aid in preventing any additional injury to a user if the bio-potential sensor is impacted, such as during a fall or other accident, as it may generally conform to the underlying portion of the body and not protrude significantly, which may, for example and without being bound to any particular theory, decrease any additional and/or intensified pressure on the body if the bio-potential sensor is impacted.

The bio-potential sensor may also include deformable and/or relatively soft components such that an impact may deform the bio-potential sensor rather than, for example, transferring force to the body of a user.

The bio-potential sensor may also generally incorporate low toxicity and/or hypoallergenic portions, such as those that contact the body of a user, e.g. the skin, such that the bio-potential sensor does not produce significant contact effects.

In some embodiments, the bio-potential sensor may be used to attach to the body of an animal, such as a human, at a high movement area, such as, for example, the scalp, and thus should resist movement on the high movement area. The bio-potential sensor may, for example, be held in place with a harness, band, cap and/or other wearable item.

In some embodiments, items may be utilized to grasp and/or attach the bio-potential sensor to the hair and/or fur of an animal, such as a human, to hold it in place. Items may include, but are not limited to, hair clips, hooks, Velcro®-type materials, elastomer materials that resist movement in hair, attachments similar to hair extensions, and/or any other appropriate items.

In some embodiments, a head band, harness and/or band for another body part may be utilized to hold a bio-potential sensor in place. For example, a pair of slots or rungs may be included such that a fabric or plastic strap may pass through. For further example, prongs or snaps may be used to connect the electrode to mating pieces on a harness. For another example, an adhesive may be used to connect the electrode to a harness. For yet another example, Velcro®-type material may be used to connect the electrode to a harness.

Figure 2:
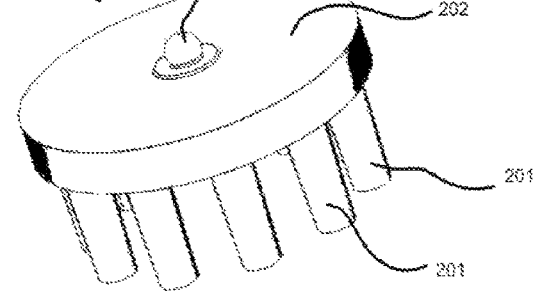
FIGS. 2 and 2a illustrate an embodiment of a bio-potential sensor with a plurality of contact leads.
Figure 2A:
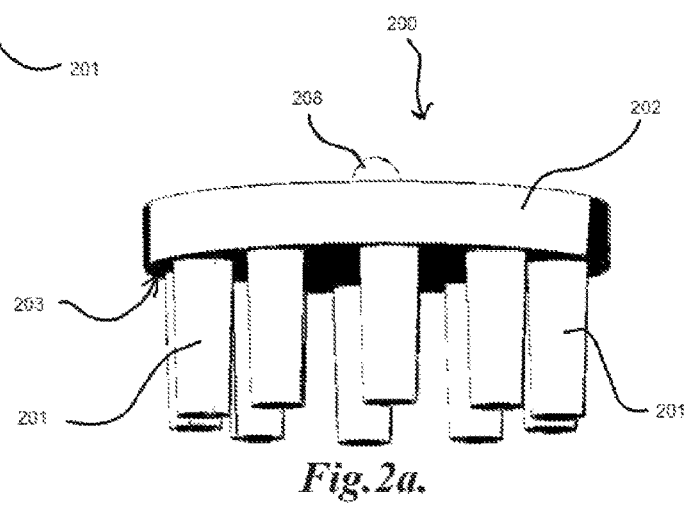

FIGS. 2 and 2a illustrate an example of a bio-potential sensor 200 which may include a plurality of leads 201 extending from a base 203. In general, the base 203 and the leads 201 may be composed of a polymeric material 202, such as those discussed above, for conducting bio-potential signals from an animal tissue. The bio-potential sensor may further include a connector 208 which may relay bio-potential signals conducted through the polymeric material 202 to an instrument for measurement and/or detection.

In some embodiments, a bio-potential sensor, such as the bio-potential sensor 200 of FIGS. 2 and 2a, may be used to contact the skin of an animal, such as a human, through hair and/or fur. In general, a plurality of leads, tines, prongs and/or other protrusions may be used to penetrate the hair and/or fur to reach the scalp and/or underlying skin, such as leads 201. The protrusions may generally exhibit spring-like behavior such that they may aid in penetration of the hair and/or fur, and in providing continuous contact with the underlying skin. The spring-like behavior may also aid in preventing movement of the bio-potential sensor. The protrusions may, for example, be formed from the same material as the base 203, such as a polymeric material 202, as discussed above. The polymeric material 202 may generally be compressible and/or deformable to provide the spring-like behavior. The protrusions themselves may also be present on cantilevered portions to provide the spring-like behavior. Such bio-potential sensors may generally be injection molded, or they may also be formed by laminating and/or coating a conductive material, such as the polymeric materials and/or metals discussed above, onto a backer which may include the three-dimensional form of the protrusions. The backer may be made by various methods, such as molding, injection molding, 3D printing and/or any other appropriate method.

In embodiments which are injection molded, the electrode may possess a higher shore A hardness and may take on a ridged structure, or it may poses a lower hardness, such as an elastomeric hardness. In higher shore A hardness embodiments, the connector portion may be made of the same material as the electrode portion.

In a lower shore A hardness embodiment, a reinforcement, such as a porous fabric reinforcing material may be encased inside of the material of the electrode to provide a mechanical strength to a grommet or snap stud used to attach the lead wire at a connector.

In some embodiments, a room temperature vulcanization silicone rubber (RTV silicone) may be used for the electrode. This may be desirable as silicone possesses natural skin-gripping and/or biocompatible properties. RTV silicone components may also be generally formed by silicone injection molding and/or by batch molding. A reinforcement, such as, for example, a porous fabric reinforcing material may be encased inside of the electrode to provide additional mechanical strength, such as to a grommet or snap stud used to attach the lead wire at a connector.

In some embodiments, the electrode may be formed as a laminated structure. For example, a pre-made conductive sheet, which may include a conductive polymeric material as discussed above, may be attached to a back with an adhesive to form the laminated structure. The conductive sheet may also be vacuum and/or thermally adhered to the backer.

The laminated structure may then be cut, such as with a die or by hand, to the appropriate size and shape for the electrode, and it may be desirable to optimize the cutting pattern to save material. The backer may also be formed as the appropriate final shape by molding and/or 3D printing, as discussed above. In general, a conductive element may be inserted and/or co-molded with the backer such that it may act as a connector and contact the conductive material of the electrode, such as with a grommet or snap stud used to attach the lead wire at a connector.

In some embodiments, the conductive polymeric material in a sheet itself may be stiff enough such that it may be directly vacuum formed onto a connector without using a backer.

In some embodiments, a metal and/or other conductive material may be coated onto a backer, as discussed above. The protrusions may generally be cantilevered and generally not deformable, such that the conductive coating may remain more intact, as such thin coatings may be more prone to cracking when the underlying material deforms. In embodiments where nickel may be utilized as a seed or base layer for plating to coat another material, it may generally be fully overcoated with the other material to avoid exposure of the nickel, since it may be harmful in direct contact with some users. In embodiments where silver is utilized, the surface of the silver may also be converted to silver chloride in order to form a silver/silver chloride type electrode, which is commonly used in EEG measurements.

Example 1

An example of a conductive thermoplastic elastomer compound based on thermoplastic polyetheramide block copolymer with carbon additives may be utilized. The compound may be injection molded without modifications using normal processing conditions as would be used with thermoplastic polyetheramide block copolymer, and can be easily overmolded or coextruded onto PA-6, PA-66, PC, PVC. The material may generally exhibit volume resistivity<70 ohm-cm and a hardness modulus of between 1.0 MPa to 7.0 MPa. The carbon additives may include: 1) carbon black or graphite—weight concentration 0.5-10%; 2) Multiwall carbon nanotube (MWCNT)—weight concentration 0-3%; 3) Single-wall carbon nanotube (SWCNT)—weight concentration 0-3%; and/or 4) Double wall carbon nanotube (DWCNT)—weight concentration 0-3%.

Example 2

An example of a highly conductive thermoplastic compound based on a low density polyethylene copolymer may be utilized. Conductivity is achieved by using a conductive form of carbon black. In addition to a low electrical resistivity, it has excellent mechanical properties and is easy to extrude or injection mold. The material may generally exhibit volume resistivity<3 ohm-cm, a hardness modulus between: 1.0 MPa and 7.0 MPa

Example 3

An example of a highly conductive thermoplastic compound based on a styrene-ethylene-butadiene-styrene TPE or (thermoplastic elastomer) SEBS filled conductive fillers with a conductive form of carbon black may be utilized. The compound can be injection molded or extruded without modifications using normal processing conditions as would be used with TPE, and may generally exhibit volume resistivity<1 ohm-cm, and a hardness modulus between: 1.0 MPa and 7.0 MPa

Example 4

An example of a bio-potential sensor used to contact the skin of an animal, such as a human, through hair and/or fur similar to the embodiment illustrated in FIGS. 2 and 2a was tested. In general, a plurality of leads, tines, prongs and/or other protrusions may be used to penetrate the hair and/or fur to reach the scalp and/or underlying skin, such as shown in with the example bio-potential sensor. The protrusions may generally exhibit spring-like behavior such that they may aid in penetration of the hair and/or fur, and in providing continuous contact with the underlying skin. The spring-like behavior may also aid in preventing movement of the bio-potential sensor. The protrusions may spread outward when pressure is applied, such as from a wearable securing. As tested, subjects do not feel the electrodes pressing against their heads as they lie in a scanner or during sleep studies and the surface contact with the scalp of the subject is increased, which offers lower contact-impedances and increased signal-to-noise ratio, such as about 10-40 kohms as tested.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention. The disclosures of all patents, patent applications and publications cited herein are hereby incorporated herein by reference in their entireties, to the extent that they are consistent with the present disclosure set forth herein.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

At least a portion of embodiments discussed herein can be implemented using a computer communicatively coupled to a network (for example, the Internet), another computer, or in a standalone computer. As is known to those skilled in the art, a suitable computer can include a central processing unit ("CPU"), at least one read-only memory ("ROM"), at least one random access memory ("RAM"), at least one hard drive ("HD"), and one or more input/output ("I/O") device(s). The I/O devices can include a keyboard, monitor, printer, electronic pointing device (for example, mouse, trackball, stylist, touch pad, etc.), or the like.

ROM, RAM, and HD are computer memories for storing computer-executable instructions executable by the CPU or capable of being complied or interpreted to be executable by the CPU. Suitable computer-executable instructions may reside on a computer readable medium (e.g., ROM, RAM, and/or HD), hardware circuitry or the like, or any combination thereof. Within this disclosure, the term "computer readable medium" or is not limited to ROM, RAM, and HD and can include any type of data storage medium that can be read by a processor. For example, a computer-readable medium may refer to a data cartridge, a data backup magnetic tape, a floppy diskette, a flash memory drive, an optical data storage drive, a CD-ROM, ROM, RAM, HD, or the like. Software implementing some embodiments disclosed herein can include computer-executable instructions that may reside on a non-transitory computer readable medium (for example, a disk, CD-ROM, a memory, etc.). Alternatively, the computer-executable instructions may be stored as software code components on a direct access storage device array, magnetic tape, floppy diskette, optical storage device, or other appropriate computer-readable medium or storage device.

Any suitable programming language can be used to implement the routines, methods or programs of embodiments of the invention described herein, including the custom script. Other software/hardware/network architectures may be used. For example, the software tools and the custom script may be implemented on one computer or shared/distributed among two or more computers in or across a network. Communications between computers implementing embodiments can be accomplished using any electronic, optical, radio frequency signals, or other suitable methods and tools of communication in compliance with known network protocols. Additionally, any signal arrows in the drawings/figures should be considered only as exemplary, and not limiting, unless otherwise specifically noted. Based on the disclosure and teachings provided herein, a person of ordinary skill in the art will appreciate other ways and/or methods to implement the invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

As used herein, "patient" or "subject" includes mammalian organisms, such as human and non-human mammals, for example, but not limited to, rodents, mice, rats, non-human primates, companion animals such as dogs and cats as well as livestock, e.g., sheep, cow, horse, etc. Therefore, for example, although the described embodiments illustrate use of the present methods on humans, those of skill in the art would readily recognize that these methods and compositions could also be applied to veterinary medicine as well as on other mammals.

The invention claimed is:

1. An injection molded or extruded bio-potential electrode composition comprising:
a thermoplastic elastomer comprising polyurethane; and
a conductive filler material comprising silver and silver chloride (Ag/AgCl) coated structures;
wherein said composition forms a solid having a hardness of between about 65 to about 95 Shore A durometer.

2. The composition of claim 1, wherein said thermoplastic elastomer and said conductive filler material are injection molded to form said bio-potential electrode composition.

3. The composition of claim 1, wherein said silver and silver chloride (Ag/AgCl) coated structures are selected from the group consisting of nano-wires, metal fibers, metal nanoparticles, metal microplates, glass and/or silica microparticles, and microplates and/or beads.

4. The composition of claim 3, wherein said composition has a volume resistivity of less than 70 ohm-cm.

5. The composition of claim 3, further comprising a cross-linking agent present in an amount to cause flocculation of said conductive filler material to form conductive pathways.

6. The composition of claim 3, wherein said composition does not contain nickel.

* * * * *